United States Patent [19]
Riffer

[11] Patent Number: 4,552,840
[45] Date of Patent: Nov. 12, 1985

[54] ENZYME ELECTRODE AND METHOD FOR DEXTRAN ANALYSIS

[75] Inventor: Richard Riffer, Crockett, Calif.

[73] Assignee: California and Hawaiian Sugar Company, San Francisco, Calif.

[21] Appl. No.: 433,255

[22] Filed: Dec. 2, 1982

[51] Int. Cl.[4] .................. C12Q 1/54; C12Q 1/34; C12Q 1/30; C12Q 1/28; C12N 11/18; C12N 11/12; C12N 11/06; C12M 1/40; C12M 1/34

[52] U.S. Cl. .................. 435/14; 435/18; 435/27; 435/28; 435/175; 435/179; 435/181; 435/288; 435/291; 435/817; 204/403; 204/415; 204/1 T

[58] Field of Search .................. 435/14, 18, 22, 27, 435/28, 175, 177, 179, 181, 188, 190, 200, 211, 288, 291, 808, 817; 204/403, 405, 1 E, 1 P

[56] References Cited

U.S. PATENT DOCUMENTS

| | | | |
|---|---|---|---|
| 2,716,237 | 8/1955 | Carlson et al. | 435/211 |
| 3,542,662 | 11/1970 | Hicks et al. | 204/1 E |
| 3,838,033 | 9/1974 | Mindt et al. | 204/403 |
| 3,847,777 | 11/1974 | Haddad et al. | 204/415 |
| 3,875,009 | 4/1975 | Glasziou et al. | 435/211 |
| 3,900,382 | 8/1975 | Brown, Jr. | 204/415 |
| 3,948,745 | 4/1976 | Guilbault et al. | 204/403 |
| 4,066,512 | 1/1978 | Lai et al. | 435/26 |
| 4,073,713 | 2/1978 | Newman | 204/1 E |
| 4,113,509 | 9/1978 | Leach et al. | 435/95 |
| 4,172,765 | 10/1979 | Keyes | 435/28 |
| 4,240,889 | 12/1980 | Yoda et al. | 204/403 |
| 4,324,257 | 4/1982 | Albarda et al. | 204/403 |
| 4,415,666 | 11/1983 | D'Orazio et al. | 204/403 |
| 4,431,507 | 2/1984 | Nankai et al. | 435/817 |
| 4,438,093 | 3/1984 | Shimada et al. | 424/94 |

OTHER PUBLICATIONS

Mattiasson, Bo, *Analytical Letters*, vol. 13(B10), pp. 851-860, 1980.

Carr, P. W. et al., *Immobilized Enzymes in Analytical and Clinical Chemistry*, John Wiley and Sons, Inc., New York, pp. 170-175 and 197-207, (1980).

*Chemical Abstracts*, vol. 92, p. 729, Abstract No. 226174w: Minami, S. et al., "Enzyme Electrode".

*Chemical Abstracts*, vol. 94, p. 114, Abstract No. 86062x: Zakharov, K. P. et al., "Polysaccharides of Diffusion Juice".

*Chemical Abstracts*, vol. 93, p. 258, Abstract No. 199797p: Mattiasson, B., "A Simple Method Involving Aqueous Two Phase Separation Systems for Activity Determination of Enzymes Hydrolyzing Macromolecular Substrates".

*Chemical Abstracts*, vol. 89, p. 101, Abstract No. 199416f: Geronimos, G. et al., "An Enzymatic Technique for the Detection of Dextran in Cane Juice and Prediction of Viscosity Increases".

*Primary Examiner*—Thomas G. Wiseman
*Assistant Examiner*—Jayme A. Huleatt
*Attorney, Agent, or Firm*—Robert G. Slick

[57] ABSTRACT

A method for the potentiometric determination of a dextran solution is provided wherein the dextran is enzymatically hydrolyzed to glucose, the glucose is oxidized to form hydrogen peroxide and the hydrogen peroxide is measured utilizing a redox electrode. A novel electrode having a plurality of enzyme impregnated layers is provided for converting the dextran to glucose.

12 Claims, 4 Drawing Figures

ENZYME ELECTRODE AND METHOD FOR DEXTRAN ANALYSIS

SUMMARY OF THE INVENTION

Dextran in raw sugar arises from infection of sugarcane by Leuconostoc bacteria, which abound in the environs of the cane fields and mills. Such contamination results in higher refining costs, reduced efficiency of refinery operations, increased sugar losses, and reduced product quality. Thus rapid and accurate dextran analysis is highly desirable in a sugar refinery.

The analysis is a relatively difficult one because of the striking diversity of structure displayed by this polysaccharide. These dissimilarities affect even those techniques ordinarily thought to be highly specific. For example, antisera produced by immunization with dextrans containing a high proportion of secondary linkages contain antibodies that precipitate these dextrans but do not react with those that are more highly 1,6-α-linked. Since all dextrans contain substantial numbers of 1,6-α linkages (by definition, at least 50%), the use of an enzyme with activity restricted to such linkages offers the prospect for greater specificity than can be achieved using other techniques. Furthermore such a method should be relatively insensitive to molecular weight, which can affect procedures that involve precipitation or light scattering. Existing procedures for such analysis are tedious and of dubious accuracy.

The present invention employs enzymes to provide a rapid, specific and sensitive potentiometric method for dextran analysis. The invention makes use of a sequentially working immobilized enzyme system in a three-layer cellulose sheath. This sandwich, overlaid on a platinum redox electrode, systematically degrades dextran and in the process produces an oxidizing species that can be detected by the electrode. Dextran is hydrolyzed stepwise to glucose, which acts as a substrate for glucose oxidase that in turn produces gluconic acid and hydrogen peroxide. The enzymes employed are readily available commercially. The preparations should in addition be free of contaminant enzymes that could impair specificity, particularly α-amylase, and—if sucrose is to be present—invertase.

Pure mold dextranase, such as that from Penicillium, is predominately endo-1,6-α-D-glucosidase, which catalyzes hydrolysis of dextran to isomaltose and higher isomaltosaccharides. Bacterial endo-dextranases yield tri-, tetra-, and pentasaccharides as the principal products; only small amounts of isomaltose are liberated so that mold dextranase is preferred.

The dextranase must be free of α-amylase activity, which would hydrolyze starch. α-Amylase also slowly attacks 1,6-α linkages in dextran, but a parallel hydrolysis of 1,4-α starch linkages by dextranase apparently does not occur.

For hydrolysis of isomaltose to glucose, the enzyme of choice is isomaltase, which, however, is not at present readily available commercially. α-Glucosidase, which is easily obtained, attacks 1,6-α bonds, albeit more slowly than the 1,4-α bonds of its normal substrate, maltose, and forms a satisfactory, readily available substitute.

The substitution of α-glucosidase for isomaltase, however, imposes restrictions on the construction and use of the dextran electrode. First, α-glucosidase is active toward sucrose. Consequently measurement must be performed on a total polysaccharide fraction, which is readily obtained by precipitation with 80% ethanol. Second, α-glucosidase catalyzes hydrolysis of starch to glucose via endwise attack. This problem can be circumvented by imposing a dialysis membrane barrier between the dextranase and the α-glucosidase. This envelope permits passage of isomaltose and isomaltosaccharides but excludes starch. An alternative found more satisfactory is pre-treatment with immobilized α-amylase. Another option is removal of sucrose and invert by dialysis or ultrafiltration.

GLUCOSE OXIDASE

The enzymatic catalysis of glucose oxidation proceeds as follows:

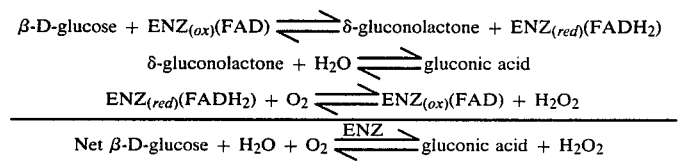

$$\beta\text{-D-glucose} + ENZ_{(ox)}(FAD) \rightleftharpoons \delta\text{-gluconolactone} + ENZ_{(red)}(FADH_2)$$

$$\delta\text{-gluconolactone} + H_2O \rightleftharpoons \text{gluconic acid}$$

$$ENZ_{(red)}(FADH_2) + O_2 \rightleftharpoons ENZ_{(ox)}(FAD) + H_2O_2$$

$$\text{Net } \beta\text{-D-glucose} + H_2O + O_2 \xrightarrow{ENZ} \text{gluconic acid} + H_2O_2$$

The glucose oxidase should be relatively free of catalase, which rapidly decomposes hydrogen peroxide, increasing its rate of disappearance by a factor of $10^{15}$.

The anomeric form of the glucose present is an important consideration. The reaction is specific for β-D glucose, which is oxidized 157 times more rapidly than the α-form. Glucose oxidase preparation frequently contain mutarotase as an impurity which permits oxidation of total α-glucose more rapidly than would spontaneous mutarotation. Highly purified samples of the oxidase may require addition of mutarotase if voltage readings are observed to drift.

A ferrocyanide/ferricyanide redox system is used as indicator of the peroxide generated. This is accomplished by adding a known excess of the reduced form to the sample to be analyzed.

DESCRIPTION OF THE PREFERRED EMBODIMENTS

Figure 1:
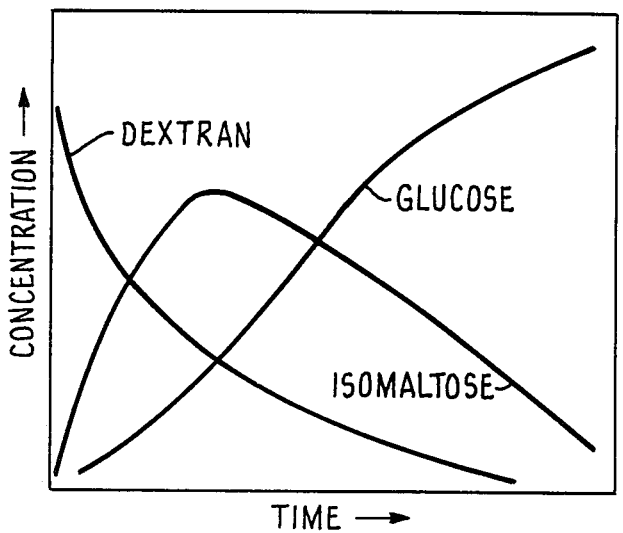
FIG. 1 is a diagram illustrating how dextran is converted to isomaltose which in turn is converted to glucose utilizing the procedure of the present invention.
Figure 2:
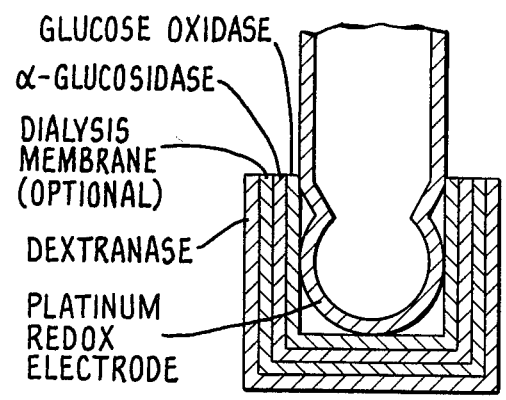
FIG. 2 is a side sectional view of a novel electrode embodying the present invention.

In order to carry out the present invention, an electrode as is shown in FIG. 2 was prepared wherein the electrode has a plurality of layers of an enzyme-impregnated material bonded onto a carrier. It has been found that a cellulose sheath made from ordinary filter paper is satisfactory for this purpose. In order to provide a stable enzyme system, the enzymes were immobilized on filter paper.

Figure 4:
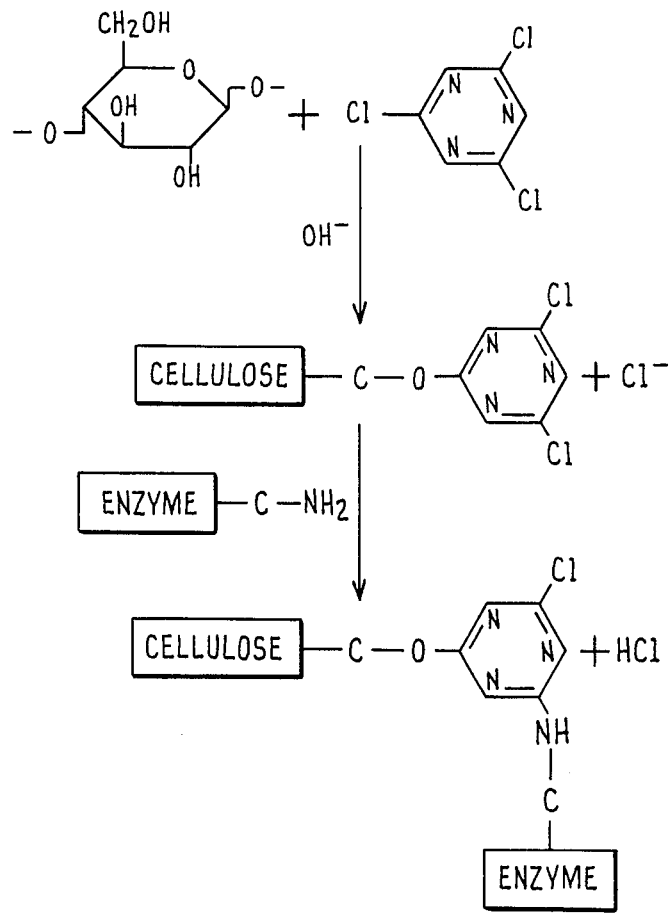
FIG. 4 illustrates the immobilization technique for bonding the enzymes to carriers.

The immobilization technique chosen was covalent bonding of enzymes to carriers via bifunctional reagents. The cellulosic carriers were activated for bonding with sym-triazine trichloride. The activated cellulose reacts with lysyl amino groups as shown in FIG. 4.

The immobilization was performed at pH 5, which is just on the alkaline side of the isoelectric points of dextranase (4.55) and glucose oxidase (4.2); thus the enzymes bear a net negative charge. In order to obtain a positively charged support to facilitate adsorption, the dichloro-sym-triazinyl cellulose can be allowed to undergo partial reaction with N-(3-aminopropyl) diethanolamine before reaction with the enzymes.

Dextranase and glucose oxidase react optimally (i.e., with their substrates) near pH 5, while $\alpha$-glucosidase exhibits maximum activity near pH 7, although such optima are often shifted by immobilization. The electrode is operated in pH 5 buffer where two of the enzymes would display maximum activity, despite the fact that $\alpha$-glucosidase is rate limiting. It should be noted that this pH does not favor rapid spontaneous mutarotation of glucose, but mutarotation is not strongly pH dependent except at high acidity or alkalinity.

Preparation of dichloro-sym-triazinyl cellulose

Patterns were cut from 9 cm. circles of Whatman no. 1 filter paper and weighed. The papers were washed and drained, then soaked in 3 M NaOH for 15 min. and the excess removed by draining. To the papers was added an equal weight of 5% (W/W) sTT in dioxanexylene (1:1 W/W). After 30 min. the excess was removed by draining, which was followed by washing for 10 min. each in (a) dioxane (twice); (b) HOAc-H$_2$O-dioxane (1:1:2 W/W/W); (c) water; and (d) acetone (twice). The papers were dried in vacuo and stored for later use. The treatment stiffens the paper considerably, probably as a result of cross-linking between cellulose chains. The papers were made slightly cationic by treatment at room temperature with 20 cc. of a solution containing 82.5 mM N-(3-aminopropyl) diethanolamine and 2.5 M NaCl. After 7.5 min., 10 cc. of 1 M HCl was added. The papers were drained, then washed with 5 M NaCl, followed by water and acetone, and replaced in the vacuum desiccator.

Preparation of immobilized enzymes

Each paper was treated with 2 cc. of 50 mM pH 5 NaOAc buffer containing 8 mg. of enzyme. After 4 hrs. at room temperature, the papers were drained and washed thoroughly with 1N NaCl and with water, to remove noncovalently bound material.

Assembly of enzyme reactor

The dried papers were assembled into open-ended boxes using epoxy and bits of waterproof tape, such as weather stripping. Openings at the base were sealed with epoxy. After drying, the boxes were fitted together. A dialysis bag (MW cutoff 14,000) with one end sealed was placed beneath the dextranase layer. The assembled sheath fit snugly over the end of the platinum redox electrode.

Immobilization of $\alpha$-amylase on alkylamine glass beads

To 100 gm. of alkylamine glass beads (Corning Glass Works, Corning, N.Y., U.S.A.) was added 150 cc. of 2.5% glutaraldehyde in 0.1 M pH 7 sodium phosphate buffer. The reaction mixture was placed in a vacuum oven at room temperature and evacuated for 1 hr. to remove air bubbles.

The mixture was then filtered with suction and washed with distilled water. One gram of $\alpha$-amylase was dissolved in the minimum amount of the pH 7 buffer and chilled in an ice bath. The glass derivative was added and the mixture was allowed to react for 4 hours. Mechanical stirring should be avoided; it grinds the glass.

The product was filtered, washed with distilled water and stored in a closed container. The product should not be frozen: the high moisture content causes the beads to crack.

Preparation of samples

Starch was removed by treatment with immobilized $\alpha$-amylase. A 40° Bx sample, 50 cc., was incubated with 2.5 gm. of $\alpha$-amylase beads for 1 hr. at 55° C. with frequent agitation, then filtered. Alternately column treatment can be used.

The polysaccharide fraction was precipitated by treating 10 cc. of the $\alpha$-amylose-processed solution with 40 cc. of abs. ethanol. A small amount of filter aid was added, and the mixture was filtered through 8$\mu$ paper, then washed with 150 cc. of 80% V/V alcohol. The polysaccharides were eluted with 95 cc. of boiling water and diluted to the mark of a 100 ml. volumetric flask.

Measurement

Calibration was made with standard dextrans measured in 0.025 M pH 5 NaOAc buffer. To each was added 1.0 cc. of 0.62 M K$_4$Fe(CN)$_6$ per 100 ml. of sample.

Samples to be measured were diluted with an equal volume of 0.05 M pH 5 NaOAc buffer, and K$_4$Fe(CN)$_6$ was added. The samples should be stirred magnetically with enough vigor for a vortex to appear: the glucose oxidase reaction requires oxygen. Between measurements the electrode is equilibrated in buffer containing ferrocyanide.

Figure 3:
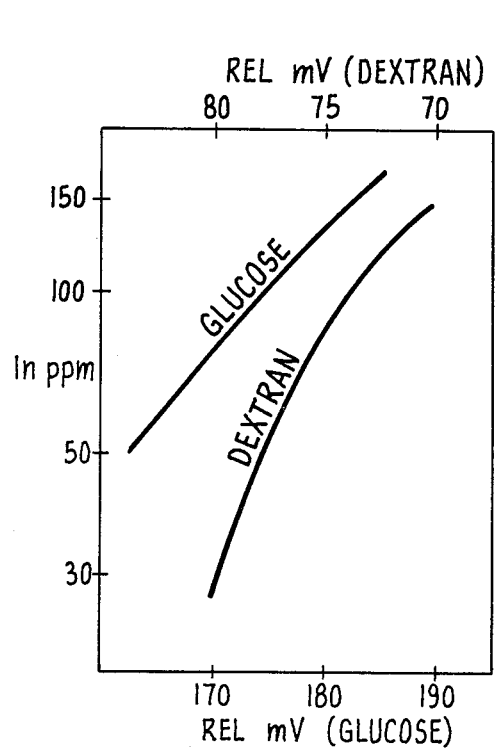
FIG. 3 is a graph of calibration curves for glucose and dextran.

There is a linear relation between the potential and the logarithm of the substrate concentration. To prepare a calibration curve, E values are plotted against concentration on semilog paper; a curve is shown in FIG. 3. The linear range for glucose is from about 50 to 150 ppm but the useful range is somewhat larger. With dextran a similar curve is obtained. The slope will vary according to the characteristic of the enzyme reactor.

The curve shown in FIG. 3 is for dextran T70 (MW 70,000), but higher molecular weight material results in an essentially identical curve. Samples with added starch, when pre-treated with immobilized $\alpha$-amylase, yielded results that could not be distinguished from starch-free samples. With sheaths constructed using a dialysis membrane, added starch had no effect on potential, but the time required to attain equilibrium was somewhat longer because of the additional diffusion burden. Glucose, maltose, or isomaltose may be determined in the presence of dextran by using an external dialysis membrane.

It is important to note that complete hydrolysis of dextran to glucose is not a requirement for useful electrode function. The immobilized enzyme system can be considered analogous to a living cell in which reactants and products are transferred by diffusion across the cell membrane. In such a flow system, after reaction has proceeded for some time, a steady state is attained. An integrated rate law can be written for such a system that is identical to that for a static system, but in which t represents contact time rather than reaction time: t is the average time that a dextran anhydroglucose unit takes to pass through the enzyme reactor, emerging as gluconic acid.

Thus the time required for analysis using the electrode is actually the time required to establish a steady state. Of course if newly released glucose is being oxidized continuously during measurement, it is necessary to record the potential reading of each sample after a definite time interval and to do likewise during calibration.

The following non-limiting examples illustrate preferred embodiments of the invention:

EXAMPLE 1

Determination of dextran in the absence of other carbohydrates

A solution was prepared of 50 mg. of dextran T70 made up to 1 l. with 0.025 M pH 5 NaOAc buffer. To 100 ml. of this solution was added 1.0 cc. of 0.62 M $K_4Fe(CN)_6$. Measurement was made using an electrode constructed without a dialysis membrane.

EXAMPLE 2

Determination of dextran in the presence of sucrose

A solution was prepared of 40 gm. of sucrose and 100 mg. of dextran T70 made up to 100 ml. The dextran was precipitated from 10 cc. of this solution by adding 40 cc. of abs. ethanol. Filter aid was added, and the mixture was filtered through an 8μ membrane, then washed with 150 cc. of 80% V/V alcohol. The dextran was eluted with 95 cc. of boiling water and made up to 100 ml. in a volumetric flask.

Fifty ml. of this solution was diluted with 50 ml. of 0.05 M pH 5 NaOAc buffer, and 1.0 cc. of ferrocyanide solution was added. Measurement was made using an electrode constructed without a dialysis membrane.

EXAMPLE 3

Determination of dextran in the presence of starch

A solution was prepared of 50 mg. dextran T70 and 50 mg. soluble potato starch made up to 1 l. with 0.025 M pH 5 NaOAc buffer. To 100 ml. of this solution was added 1.0 cc. of ferrocyanide solution. Measurement was made using an electrode constructed with a dialysis membrane.

EXAMPLE 4

Determination of dextran in the presence of starch

A solution was prepared containing 100 mg. each of dextran T70 and soluble potato starch made up to 100 ml. Fifty cc. of this solution was incubated with 2.5 gm. of α-amylase beads for 1 hr. at 55° C. with frequent agitation, then filtered. The dextran was isolated by precipitation according to the procedure in Example 2. Measurement was made with an electrode constructed without a dialysis membrane.

EXAMPLE 5

Determination of dextran in the presence of starch and sucrose

A solution was prepared containing 100 mg. each of dextran T70 and soluble potato starch, and 40 gm. of sucrose made up to 100 ml. The starch and sucrose were eliminated and the dextran measured according to the procedure in Example 4.

I claim:

1. An electrode for the potentiometric determination of dextran in a solution comprising a platinum redox electrode, a first cellulose absorbent sheath surrounding the electrode with immobilized glucose oxidase, a second absorbent sheath thereover with immobilized enzymes selected from the group consistinng of α-glucosidase and isomaltase, with the provision that a means for excluding compounds having a molecular weight of 14,000 or greater surrounding said second sheath is included when α-glucosidase is selected and when the solution contains starch and an outer absorbent sheath with immobilized dextranase surrounding said means wherein the amounts of glucose oxidase, α-glucosidase or isomaltase and dextranase are sufficient to determine the amount of dextran.

2. The electrode of claim 1 wherein said means is a dialysis membrane.

3. The electrode of claim 1 wherein α-glucosidase is selected.

4. The electrode of claim 1 wherein isomaltase is selected.

5. The electrode of claim 1 wherein each sheath is made from a cellulose filter paper sheet.

6. The electrode of claim 5 wherein each enzyme is immobilized on cellulose by covalent bonding utilizing a bifunctional reagent.

7. The electrode of claim 6 wherein the bifunctional reagent is sym-triazine trichloride.

8. The electrode of claim 1 wherein the dextranase is mold dextranase.

9. A method for the potentiometric determination of a dextran in a solution comprising immersing into a sample, an electrode containing a platinum redox electrode, a first cellulose absorbent sheath surrounding the electrode with immobilized glucose oxidase, a second absorbent sheath thereover with immobilized enzymes selected from the group consisting of α-glucosidase and isomaltase, with the provision that a means for excluding compounds having a molecular weight of 14,000 or greater surrounding said second sheath is included when α-glucosidase is selected and when the solution contains starch and an outer absorbent sheath with immobilized dextranase surrounding said means wherein the amounts of glucose oxidase, α-glucosidase or isomaltase and dextranase are sufficient to determine the amount of dextran, incubating and measuring the voltage which correlates with the amount of dextran present.

10. The method of claim 9 wherein α-glucosidase is selected.

11. The method of claim 9 wherein isomaltase is selected.

12. The method of claim 9 wherein said means is a dialysis membrane.

* * * * *